US009271987B2

(12) United States Patent
Zhong et al.

(10) Patent No.: US 9,271,987 B2
(45) Date of Patent: Mar. 1, 2016

(54) METHODS AND COMPOSITIONS FOR TREATING ALZHEIMER'S DISEASE

(71) Applicant: Cold Spring Harbor Laboratory, Cold Spring Harbor, NY (US)

(72) Inventors: Yi Zhong, Huntington, NY (US); Hsueh-cheng Chiang, Gaithersburg, MD (US); Lei Wang, Beijing (CN)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 13/949,403

(22) Filed: Jul. 24, 2013

(65) Prior Publication Data

US 2013/0302337 A1 Nov. 14, 2013

Related U.S. Application Data

(63) Continuation of application No. PCT/US2012/022646, filed on Jan. 26, 2012.

(60) Provisional application No. 61/436,363, filed on Jan. 26, 2011.

(51) Int. Cl.

*A61K 39/395* (2006.01)
*A61K 31/5377* (2006.01)
*A61K 31/517* (2006.01)

(52) U.S. Cl.

CPC .......... *A61K 31/5377* (2013.01); *A61K 31/517* (2013.01)

(58) Field of Classification Search

None

See application file for complete search history.

(56) References Cited

U.S. PATENT DOCUMENTS 7,449,442 B2 11/2008 He et al.
2003/0194403 A1 10/2003 Van de Winkel et al.
2003/0232741 A1 12/2003 Neufeld et al.

FOREIGN PATENT DOCUMENTS

WO WO 03/068147 A2 8/2003
WO 2007/008338 A1 1/2007
WO WO 2008/003317 A1 1/2008
WO 2010-048446 A2 4/2010

OTHER PUBLICATIONS

Birnbaum, A. et al., "Gefitinib therapy for non-small cell lung cancer" Current Treatment Options in Oncology (Jan. 2005) pp. 75-81, vol. 6, No. 1.

Ceresoli, G.L. et al., "Gefitinib in patients with brain metastases from non-small-cell lung cancer: a prospective trial" Annals of Oncology (2004) pp. 1042-1047, vol. 15.

Chiang, H.C. et al., "Distinctive Roles of Different β-amyloid 42 Aggregates in Modulation of Synaptic Functions" The FASEB Journal (Jun. 2009) pp. 1969-1977, vol. 23.

Chiang, H.C. et al., "PI3 Kinase Signaling is Involved in Aβ-Induced Memory Loss in *Drosophilia*" PNAS (Apr. 13, 2010) pp. 7060-7065, vol. 107, No. 15.

Cohen, E. et al., "Reduced IGF-1 Signaling Delays Age-Associated Proteotoxicity in Mice" Cell (Dec. 11, 2009) pp. 1157-1169, vol. 139.

Dahlgren, K.N., et al., "Oligomeric and Fibrillar Species of Amyloid-β Peptides Differentially Affect Neuronal Viability" The Journal of Biological Chemistry (Aug. 30, 2002) pp. 32046-32053, vol. 277, No. 35.

Gschwind, A. et al., "The discovery of receptor tyrosine kinases: targets for cancer therapy" Nature Reviews Cancer (May 2004) pp. 361-370, vol. 4, No. 5.

Heimberger, A.B. et al., "Brain Tumors in Mice are Susceptible to Blockade of Epidermal Growth Factor Receptor (EGFR) with the Oral, Specific, EGFR-Tyrosine Kinase Inhibitor ZD1839 (Iressa)" Clinical Cancer Research (Nov. 2002) pp. 3496-3502, vol. 8.

Iijima, K. et al., "Ab42 Mutants with Different Aggregation Profiles Induce Dstinct Pathologies in *Drosophilia*" PLoS ONE (Feb. 2008) pp. 1-8, vol. 3, No. 2, e1703.

Iijima, K. et al., "Dissecting the pathological effects of human Aβ40 and Aβ42 in *Drosophila*: A potential model for Alzheimer's Disease" PNAS (Apr. 27, 2004) pp. 6623-6628, vol. 101, No. 17.

Jankowsky, J.L. et al., "Environmental Enrichment Mitigates Cognitive Deficits in a Mouse Model of Alzheimer's Disease" The Journal of Neuroscience (May 25, 2005) pp. 5217-5224, vol. 25, No. 21.

Jankowsky, J.L. et al., "Co-expression of Multiple Transgenes in Mouse CNS: a comparison of strategies" Biomolecular Engineering (2001) pp. 157-165, vol. 17.

Jensen, M.T. et al., "Lifelong immunization with human B-amyloid (1-42) protects Alzheimer's transgenic mice against cognitive impairment throughout aging" Neuroscience (2005) pp. 667-684, vol. 130, No. 3.

Laurén, J. et al., "Cellular Prion Protein Mediates Impairment of Synaptic Plasticity by Amyloid-β Oligomers" Nature (Feb. 26, 2009) pp. 1128-1132, vol. 457.

Martinez-Coria, H. et al., "Memantine Improves Cognition and Reduces Alzheimer's-Like Neuropathology in Transgenic Mice" The American Journal of Pathology (Feb. 2010) pp. 870-880, vol. 176, No. 2.

Reiserer, R.S., et al., "Impaired spatial learning in the APPSwe+PSEN1ΔE9 bigenic mouse model of Alzheimer's disease" Genes, Brain and Behavior (2007) pp. 54-65, vol. 6.

Rojas, M., et al., "Controlling Epidermal Growth Factor (EGF)-stimulated Ras Activation in Intact Cells by a Cell-permeable Peptide Mimicking Phosphorylated EGF Receptor" The Journal of Biological Chemistry (Nov. 1996) pp. 27456-27461, vol. 271, No. 44, issue of Nov. 1.

Savonenko, A. et al.,"Episodic-like memory deficits in the APPswe/PS1dE9 mouse model of Alzheimer's disease: relationships to (beta)-amyloid deposition and neurotransmitter abnormalities" Neurobiol Dis (Apr. 2005) pp. 602-617, vol. 18, No. 3.

Scholtzova, H. et al., "Memantine leads to behavioral improvement and amyloid reduction in Alzheimer's-disease-model transgenic mice shown as by micromagnetic resonance imaging" Journal of Neuroscience Research (Sep. 2008) pp. 2784-2791, vol. 86, No. 12.

Tully, T. et al., "Classical Conditioning and Retention in Normal and Mutant *Drosophila melanogaster*" Journal of Comparative Physiology A (1985) pp. 263-277, vol. 157, No. 2.

(Continued)

*Primary Examiner* — Olga N Chernyshev

(74) *Attorney, Agent, or Firm* — Scully Scott Murphy & Presser

(57) ABSTRACT

This disclosure relates to methods and compositions useful for treating Alzheimer's disease. In particular, the disclosure relates to pharmaceutical compositions containing an EGFR-inhibitory compound suitable for administration to treat Alzheimer's disease, as well as to related therapeutic methods. In addition, this disclosure relates to screening methods for identifying compounds useful for treating Alzheimer's disease based on the ability to inhibit the activity of EGFR.

3 Claims, 6 Drawing Sheets

(56) References Cited

OTHER PUBLICATIONS

Wakeling, A.E. et al., "ZD1839 (Iressa): An Orally Active Inhibitor of Epidermal Growth Factor Signaling with Potential for Cancer Therapy" Cancer Res (Oct. 15, 2002) pp. 5749-5754, vol. 62.

International Search Report and Written Opinion dated Aug. 22, 2012 issued in International Application No. PCT/US2012/022646.

Sharma, S.V. et al., "Epidermal Growth Factor Receptor Mutations in Lung Cancer" Nature Reviews Cancer (Mar. 2007) pp. 169-181, vol. 7.

"Epidermal Growth Factor Receptor" from Wikipedia, the free encyclopedia, http://en.wikipedia.org/wiki/Epidermal__growth__factor__receptor, dated Jan. 11, 2011, pp. 1-10.

Franke, T.F., "PI3K/Akt: Getting it Right Matters" Oncogene (2008) pp. 6473-6488, vol. 27.

Fan, Q.W. et al., "Targeting the RTK-PI3K Axis in Malignant Glioma: Overcoming Resistance" Current Top Microbiol. Immunology (2010) pp. 279-296, vol. 347.

Bunney, T. D. et al., "Phosphoinositide Signaling in Cancer: Beyond PI3K and PTEN" Nature Reviews Cancer (May 2010) pp. 342-352, vol. 10.

Almeida, C.G., et al., "β-Amyloid Accumulation Impairs Multivesicular Body Sorting by Inhibiting the Ubiquitin-Proteasome System", The Journal of Neuroscience, (Apr. 19, 2006), vol. 26, No. 16, pp. 4277-4288.

Jacobsen, S., et al., "P2-302: GSI-953 is a potent APP-selective gamma-secretase inhibitor for the treatment of Alzheimer's disease", Alzheimer's & Dementia: The Journal of the Alzheimer's Association, (Jul. 1, 2008), vol. 4, No. 4, p. T461.

Extended Supplementary European Search Report dated Feb. 26, 2015 issued in corresponding European Patent Application No. EP 12 73 9544.

English-language translation only of Chinese Office Action dated Feb. 25, 2015 issued in corresponding Chinese Patent Application No. 201280015493.5.

Supplementary Partial European Search Report dated Nov. 27, 2014 issued in corresponding European Patent Application No. EP 12 73 9544.

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1

aatagagaac ggcaggagca                                                  20


<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2

gccatgaggg cactaatcat                                                  20


<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3

aggactgacc actcgaccag                                                  20


<210> SEQ ID NO 4
<211> LENGTH: 19
```

-continued

```
<212> TYPE: DNA
<213> ORGANISM: Artificial Sequence
<220> FEATURE:
<223> OTHER INFORMATION: Synthetic Oligonucleotide

<400> SEQUENCE: 4

cgggggtcta gttctgcat                                              19
```

METHODS AND COMPOSITIONS FOR TREATING ALZHEIMER'S DISEASE

CROSS REFERENCE TO RELATED APPLICATIONS

The present application claims benefit from International Application No. PCT/US12/022,646, filed on Jan. 26, 2012, which claims benefit from U.S. Provisional Application No. 61/436,363 filed on Jan. 26, 2011, the entire contents and disclosures of which are incorporated herein by reference.

FIELD OF THE DISCLOSURE

This disclosure relates to methods and compositions useful for treating Alzheimer's disease. In particular, the disclosure relates to pharmaceutical compositions containing an EGFR-inhibitory compound suitable for administration to treat Alzheimer's disease, as well as to related therapeutic methods. In addition, this disclosure relates to screening methods for identifying compounds useful for treating Alzheimer's disease based on the ability to inhibit the activity of EGFR.

INCORPORATION BY REFERENCE OF SEQUENCE LISTING

The Sequence Listing in an ASCII text file, named as 27092Z_SEQ.txt of 2 KB, created on Jul. 23, 2013, and submitted to the United States Patent and Trademark Office via EFS-Web, is incorporated herein by reference.

BACKGROUND ART

A *Drosophila* model of Alzheimer's disease (AD) has been reported (Iijima et al., *PNAS* 101 (17): 6623-6628, 2004; Iijima et al., *PLoS ONE* 3(2): e1703, 2008), in which pan-neuronal expression of a secretary form of Aβ42 leads to phenotypes that recapitulate major features of AD clinical symptoms, including age-dependent memory loss, neurodegeneration, and accumulation of Aβ deposits. A subsequent study of synaptic plasticity in the *Drosophila* model of AD has revealed that long-term depression (LTD) is affected due to expression of Aβ42 (Chiang et al., *FASEB J.* 23: 1969-1977, 2009). A separate study also suggests that Aβ42-induced LTD resulted from an altered PI3 kinase activity (Chiang et al., *PNAS* 107: 7060-7065, 2010).

SUMMARY OF THE DISCLOSURE

In one aspect, this disclosure is directed to a method of treating Alzheimer's disease in a subject by administering an effective amount of an EGFR inhibitor to the subject. EGFR inhibitors can be a polypeptide (such as a soluble form of EGFR or an anti-EGFR antibody), or a small molecule. Suitable small molecule EGFR inhibitors for use in the method of this disclosure include Gefitinib, Erlotinib, EKB-569, CL-387,785, Lapatinib, Canertinib, HKI-272, BIBW 2992, HKI-357, ZD-6474, AEE 788, XL647, BMS-599626, IPI-504, and 17-AAG.

In another aspect, this disclosure is directed to a pharmaceutical composition containing an EGFR inhibitor in an amount effective for treating Alzheimer's disease, and a pharmaceutically acceptable carrier.

In a further aspect, this disclosure is directed to a screening assay for identifying compounds useful for treating Alzheimer's disease. The assay includes exposing cultured cells of a cell line which expresses human EGFR on the cell surface to Aβ42 oligomers in the presence of a candidate compound and in the absence of a candidate compound, respectively, and comparing the level of EGFR activation in cells exposed to Aβ42 oligomers in the presence of the candidate compound with that in the absence of the candidate compound, wherein a reduction in the level of EGFR activation indicates the usefulness of the candidate compound to treat Alzheimer's disease.

DETAILED DESCRIPTION

Figure 1:
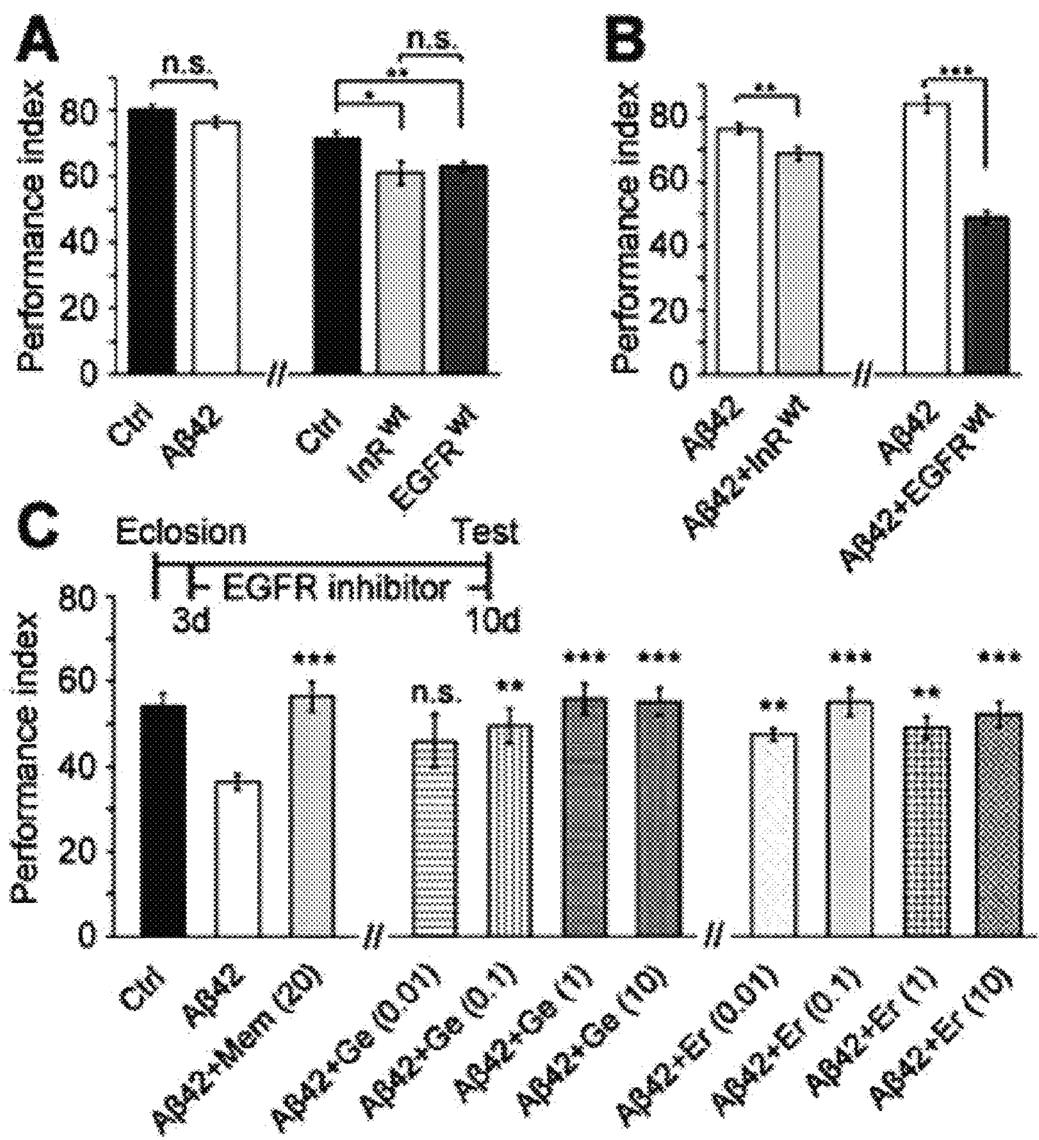
FIG. 1A-C. Identification of the involvement of EGFR in Aβ42-induced immediate memory loss in *Drosophila*. (A) In 5-day old adult female flies, no memory effects observed in Aβ42-expressing flies, but slight defect due to pan-neuronal expression of either InR or EGFR (elav/+; UAS-$InR^{wt}$/+ or elav/+; UAS-$EGFR^{wt}$/+). N=10-13. All data, otherwise indicated, are expressed as means±s.e.m and for t test: *p<0.05, p<0.01, *p<0.001. (B) Synergistic effect of EGFR, but not InR, on Aβ42-induced memory loss (elav/+; UAS-Aβ42/+; UAS-$EGFR^{wt}$/+ and elav/+; UAS-Aβ42/UAS-In-$R^{wt}$). N=14-29. (C) Rescue of Aβ42-induced memory loss. Top panel: Drug-feeding paradigm for this and following figures are the same as illustrated. Lower panel: The histogram represents immediate memory for effects of drug feeding. Drug concentrations (in μg/ml) are as indicated in bracket and the control is treated with sucrose. Mem: memantine; Ge: Gefitinib; Er: erlotinib. N=8 for each group.

It has been demonstrated herein that the egfr gene interacted with the toxicity of Aβ42 genetically. It has also been demonstrated herein that two EGFR inhibitory compounds, Gefitinib (Ge) and erlotinib (Er), which have been approved for use in treatment of cancers in human patients, could rescue Aβ42-induced age-dependent memory loss in a *Drosophila* AD model. Further, it has been demonstrated herein that Ge also rescued memory loss in a mouse model of AD. In addition, it has been demonstrated herein that Aβ42 increased the phosphorylation and activation of EGFRs in COS-7 cells, and that Aβ42 molecules were immunoprecipitated with EGFRs.

Accordingly, this disclosure provides methods and compositions useful for treating Alzheimer's disease. Additionally, this disclosure provides a method for screening for compounds effective for treating Alzheimer's disease.

Pharmaceutical Compositions

In one aspect, this disclosure is directed to pharmaceutical compositions useful for treating Alzheimer's disease.

As used herein, "treating Alzheimer's disease" means herein delaying the onset, slowing down the progression, and/or ameliorating the symptoms of the disease.

Alzheimer's disease is the most common form of dementia, and its symptoms are well recognized clinically. Early stage symptoms include inability to acquire new memories, for example, difficulty in recalling recent events and inability to acquire new information. As the disease progresses, the impairment of learning and memory becomes more pronounced, symptoms can include language impairment (including speech difficulties, and loss of reading and writing skills), loss of long term memory, loss of motor coordination, and behavioral and neuropsychiatric symptoms such as confusion, irritability, aggression, mood swings and general withdrawal. Advanced stage is characterized by the loss of verbal language ability, deterioration of muscle mass and mobility, and loss of other bodily functions.

By "delaying" the onset of Alzheimer's disease, it is meant that the pharmaceutical compositions and therapeutic methods provided herein can postpone, hinder, or slow the development of the disease such that the probability of early disease symptoms manifesting in a subject, or the probability of the occurrences of the disease among multiple subjects, within a given time frame, is reduced when compared to not using the compositions or methods provided herein.

By "slowing down the progression" of Alzheimer's disease, it is meant that the pharmaceutical compositions and therapeutic methods provided herein effectively inhibit the progressive decline of the learning, memory, or language ability or other bodily functions.

By "ameliorating the symptoms" of the disease, it is meant that the pharmaceutical compositions and therapeutic methods provided herein reduce disease symptoms, and/or improve the learning, memory, or language ability or other bodily functions.

The term "subject" as used herein refers to any mammalian subject. In one embodiment, the subject is a human subject.

In accordance with the instant disclosure, pharmaceutical compositions useful for treating Alzheimer's disease contain an EGFR inhibitor.

As used herein, "an EGFR inhibitor" refers to a molecule that inhibits the activity of EGFR. EGFR, also known as ErbB1 or HER1, is a member of the ErbB family receptors, a subfamily of the receptor tyrosine kinase (RTK) super-family of cell surface receptors which are mediators of cell signaling in response to extra-cellular growth factors. EGFR is activated upon binding by its ligand, including epidermal growth factor (EGF) and transforming growth factor α (TGFα), which results in the formation of active homodimers and in some instances, heterodimers with another member of the ErbB receptor family. Dimerization activates the intrinsic protein-tyrosine kinase activity, leading to autophosphorylation of several tyrosine residues in the cytoplasmic domain of EGFR, which in turn activates downstream signaling cascades through other proteins having phosphotyrosine-binding SH2 domains.

As shown herein, Aβ42, especially an oligomeric form of Aβ42, also triggers activation and phosphorylation of EGFR, and the activation is believed to result from direct binding of EGFR by Aβ42.

EGF receptors are well conserved structurally and functionally across species. The term "EGFR" is used to generically refer to an EGF receptor from any animal species. In specific embodiments, the EGFR is a mammalian EGFR, particularly human EGFR.

The activity of EGFR can be conveniently measured in a cultured cell line, for example, based on the level of EGFR phosphorylation upon binding to exogenously applied EGF or Aβ42. Cell lines suitable for use can be a mammalian, insect or yeast cell line, among others, which expresses EGFR endogenously, or is transfected to express an EGFR molecule of interest, e.g., human EGFR. Examples of suitable cell lines include S2, COS-7, SH-HY5Y, HEK-293, NIH 3T3, and Hela, among others. In a specific embodiment, the COS-7 cell line (derived from monkey kidney) transfected with the human egfr gene is used for determining the EGFR activity.

Phosphorylation of EGFR at one or more of the tyrosines, i.e., Y992, Y1045, Y1068, Y1148 and Y1173, can be detected, e.g., in a Western blot using phosphotyrosine-specific antibodies, and the detected signals can be quantified using methods and software available in the art. In some embodiments, phosphorylation of EGFR at Y1068 is detected and quantified as a measure of the level of activation of EGFR.

Inhibition of EGFR activity by a specific molecule can be determined by comparing the EGFR activity in the presence of the molecule with the EGFR activity in the absence of the molecule, wherein a reduction in the activity indicates inhibition. Inhibition is significant when the EGFR activity is reduced by at least 20%, 30%, 40%, 50%, 60%, 70%, 80%, 90% or more, in the presence of an inhibitor as compared to in the absence of the inhibitor.

According to the present disclosure, the inhibitors can be polypeptides, such as a soluble form of EGFR (e.g., polypeptides composed of the extracellular domain of EGFR or an EGF-binding segment thereof), or antibodies directed to the extracellular domain of EGFR, including polyclonal antibodies and monoclonal antibodies such as humanized monoclonal antibodies.

The inhibitors can be small molecule compounds as well. By "small molecule compounds" it is meant small organic compounds or salts thereof, generally having a molecule weight of less than 1500 daltons, preferably less than 1000 daltons, more preferably less than 800 daltons. Small molecule EGFR inhibitors suitable for use in the pharmaceutical compositions of this disclosure include those that have documented in the art and developed for treating cancers. Further, small molecule EGFR inhibitors suitable for use in the pharmaceutical compositions of this disclosure also include compounds which are confirmed or newly identified as EGFR inhibitors by the screening assay disclosed herein.

In some embodiments, the small molecule EGFR inhibitors are selected from Gefitinib (Iressa; N-(3-chloro-4-fluorophenyl)-7-methoxy-6-(3-morpholin-4-ylpropoxy)quinazolin-4-amine), Erlotinib (Tarceva; N-(3-ethynylphenyl)-6,7-bis(2-methoxyethoxy)quinazolin-4-amine), EKB-569 (4-(3-bromoanilino)-6,7-dimethoxy-3-quinolinecarbonitrile), CL-387,785 (N-[4-[(3-Bromophenyl)amino]-6-quinazolinyl]-2-butynamide), Lapatinib (GW572016; Tykerb; N-[3-chloro-4-[(3-fluorophenyl)methoxy]phenyl]-6-[5-[(2-methylsulfonylethylamino)methyl]-2-furyl]quinazolin-4-amine), Canertinib (CI-1033; PD183805; N-[4-(3-Chloro-4-fluorophenylamino)-7-[3-(4-morpholinyl)propoxy]quinazolin-6-yl]-2-propenamide dihydrochloride), HKI-272 (Neratinib, or (2E)-N-[4-[[3-chloro-4-[(pyridin-2-yl)methoxy]phenyl]amino]-3-cyano-7-ethoxyquinolin-6-yl]-4-(dimethylamino)but-2-enamide), BIBW 2992 (Afatinib, N-[4-[(3-Chloro-4-fluorophenyl)amino]-7-[[(3S)-tetrahydro-3-furanyl]oxy]-6-quinazolinyl]-4-(dimethylamino)-2-butenamide), HKI-357 (Wyeth, (E)-N-[4-[3-Chloro-4-[(3-fluorobenzyl)oxy]anilino]-3-cyano-7-ethoxy-6-quinolinyl]-4-(dimethylamino)-2-butenamide), ZD-6474 (Vandetanib, N-(4-bromo-2-fluorophenyl)-6-methoxy-7-[(1-methylpiperidin-4-yl)methoxy]quinazolin-4-amine), AEE 788 (Novartis, (R)-6-(4-((4-ethylpiperazin-1-yl)methyl)phenyl)-N-(1-phenylethyl)-7H-pyrrolo[2,3-d]pyrimidin-4-amine), XL647 (Exelexis), BMS-599626 (Bristol-Myers Squibb, [4-[[1-(3-fluorophenyl)methyl]-1H-indazol-5-ylamino]-5-methylpyrrolo[2,1-f][1,2,4]triazin-6-yl]carbamic Acid, (3S)-3-Morpholinylmethyl Ester.), IPI-504 (Infinity Pharmaceuticals, 17-Allylamino-17-demethoxygeldanamycin Hydroquinone Hydrochloride), 17-AAG (Kosan, 17-(allylamino)-17-demeth-oxygeldanamycin), pharmaceutically acceptable salts thereof, or a combination thereof.

In a specific embodiment, the small molecule EGFR inhibitor is Gefitinib or Erlotinib, or a combination of the two.

In addition to an EGFR inhibitor, the pharmaceutical composition of this disclosure can include a pharmaceutically acceptable carrier. Pharmaceutically acceptable carriers include solvents, dispersion media, isotonic agents and the like. Except insofar as any conventional media, agent, diluent or carrier is detrimental to the recipient or to the therapeutic effectiveness of the active ingredients contained therein, its use is appropriate. The carrier can be liquid, semi-solid, e.g. pastes, or solid carriers. Examples of carriers include oils, water, oil/water emulsions, saline solutions, alcohol, sugar, gel, lipids, liposomes, resins, porous matrices, binders, fillers, coatings, preservatives and the like, or combinations thereof.

Active ingredients can be combined with a carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like, using conventional formulation methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Therapeutic Methods

In a further aspect, this disclosure is directed to a method of treating Alzheimer's disease by administering a pharmaceutical composition described hereinabove, which contains a therapeutically effective amount of an EGFR inhibitor.

The term "therapeutically effective amount" means the amount required to achieve beneficial results in treating Alzheimer's disease as defined herein, i.e., to delay the onset, slow down the progression or ameliorate the symptoms of the disease, after given to the recipient for an appropriate period of time.

The precise amount of a pharmaceutical composition to be therapeutically effective may vary, depending on the nature of the active ingredient, the health and conditions of the recipient, and the route of administration, but can be determined by a skilled practitioner. It has been demonstrated herein that the concentrations of Ge effective to rescue memory loss are one hundred to one thousand times lower than the concentrations used for treating cancer.

For example, in some embodiments, the method provided herein for treating Alzheimer's disease involves administration to a patient of Ge at an amount ranging from 0.5 to 100 mg/day/person, and in some embodiments, from 1 to 50 mg/day/person, for example, 1, 5, 10, 15, 20 and 25 mg/day/person, or an amount between any of the two values listed above.

The pharmaceutical composition can be given once or multiple times daily, every other day, or any other appropriate dosing schedule, and can be administered to the subject by any appropriate route, including the oral, parenteral (e.g., intravenous, intraperitoneal, intradermal, subcutaneous or intramuscular), intracranial, intracerebral, or intraspinal route.

Screening Assay

In still another aspect, this disclosure provides a screening assay for identifying compounds suitable for use to treat Alzheimer's disease. This screening assay is designed based on the unique recognition disclosed herein that Aβ42 activates EGFR through direct binding, which then activates downstream signaling pathways, which in turn negatively impact synaptic plasticity that ultimately causes memory loss. Hence, candidate compounds, e.g., compounds in a combinatorial library, are screened for their ability to interfere with the Aβ42-mediated EGFR activation.

The screening assay of this disclosure employs a cell line in culture, and determines the effect of a compound on EGFR activation in the cultured cells in response to exogenously applied Aβ42.

Cell lines suitable for use in the screening assay can be a mammalian, insect or yeast cell line, among others, which expresses EGFR endogenously, or is transfected to express an EGFR molecule of interest, e.g., human EGFR. Examples of suitable cell lines include S2, COS-7, SH-HY5Y, HEK-293, NIH 3T3, and Hela, among others. In a specific embodiment, the COS-7 cell line (derived from monkey kidney) transfected with the human egfr gene is used in the assay.

Aβ42 oligomers or a preparation enriched in Aβ42 oligomers can be added to the cell culture at a concentration in the range of about 0.5 to about 20 μM, in some embodiments, 1 to 10 μM, and in specific embodiments, about 5 μM. Both synthetic and recombinantly produced Aβ42 peptides can be used to make Aβ42 oligomers.

EGFR activation can be determined based on the level of EGFR phosphorylation. For example, phosphorylation of EGFR at one or more of the tyrosines, i.e., Y992, Y1045, Y1068, Y1148 and Y1173, can be detected, e.g., in a Western blot using phosphotyrosine-specific antibodies, and the detected signals can be quantified using methods and software available in the art. In some embodiments, phosphorylation of EGFR at Y1068 is detected and quantified as a measure of the level of activation of EGFR.

Compounds that reduce Aβ42-induced EGFR activation can therefore be identified. Such compounds can be further tested in animal models of Alzheimer's disease to confirm their utility and efficacy.

Example 1

Materials And Methods

*Drosophila* Stocks

Human wild type Aβ42 transgenic fly (UAS-Aβ42) used herein has been previously described (Iijima et al., *PLoS ONE* 3(2): e1703, 2008). UAS-InR$^{wt}$ and UAS-EGFR$^{wt}$ were obtained from the Bloomington *Drosophila* Stock Center (Indiana, USA). elav$^{C155}$-Gal4 is a lab stock. Flies were raised and maintained at room temperature (22-24° C.). All stocks used for Pavlovian olfactory conditioning were equilibrated by five generations of out-cross to w$^{1118}$ (isoCJ1).

Pavlovian Olfactory Associative Immediate Memory

The training and testing procedures were the same as previously described (Tully and Quinn, *J Comp Physiol A* 157: 263-277, 1985). During one training session, a group of 100 flies was sequentially exposed for 60 seconds to two odors, 3-octanol (OCT, Fluka) or 4-methylcyclohexanol (MCH, Fluka), with 45 seconds of fresh air in between. Flies were subjected to foot-shock (1.5 seconds pulses with 3.5 seconds intervals, 60 V) during exposure to the first odor (CS+) but not to the second (CS−). To measure "immediate memory" (also referred to as "learning"), flies were transferred immediately after training to the choice point of a T-maze and forced to choose between the two odors for 2 min. Then flies were trapped in their respective T-maze arms, anesthetized, and counted. A performance index (PI) was calculated from the distribution of this group of flies in the T-maze. A reciprocal group of flies was trained and tested by using OCT as the CS+ and MCH as the CS+, respectively. The so-called half-PIs, (OCT) and PI (MCH), were finally averaged for an n=1 and multiplied by 100. A PI of 0 indicated a distribution of 50:50 (no learning), while a PI of 100 indicated "perfect learning" that 100% of the flies avoided the CS+ previously paired with foot shock. Control groups are age-matched to the experimental groups in each test. For drug feeding treatments on flies, Gefitinib and Erlotinib (LC Laboratories) were dissolved in dimethyl sulfoxide (DMSO, Sigma) and stored in −20° C. Flies were starved for 3 hours in empty vials, and then fed with drugs, diluted in 4% sucrose, for another 4 hours. Flies were transferred to normal food after treatment. Drug feeding was carried out once each day during the treatment period. 20 μg/ml Memantine (Sigma) was used as a positive control.

Preparation of Aβ42 Oligomers

The preparation procedure was described previously (Dahlgren K, et al., *J Biol Chem.* 277:32046-53, 2002). Synthetic and recombinant wild type Aβ42 (AnaSpec, Inc.) was initially dissolved to 1 mM in hexafluoroisopropanol (Sigma). Hexafluoroisopropanol was removed under vacuum in a Speed Vac, and the peptide film was stored at −20° C. For oligomer preparation, the peptide was first resuspended in DMSO to a concentration of 12.5 mg/ml and then diluted with DMEM/F-12 (phenol red-free, Invitrogen) to a final concentration of 500 μg/ml and incubated at 4° C. for 24 h. Oligomers were detected by Western blot.

Cell Culture, Transfection and Oligomer Treatment

COS-7 cells were cultured in normal Dulbecco's Modified Eagle Medium (D-MEM) containing 10% fetal bovine serum (Invitrogen) at 37° C. in 5% $CO_2$. Human wild type Aβ42 plasmid is a lab stock. Human EGFR$^{wt}$ and EGFR$^{K721A}$ plasmids were provided by Dr. Parsons. Transfection as performed following the Lipofectamine 2000 manuals (Invitrogen). After 48 h, cells were washed with fresh medium once and incubated with 10 or 25 μg/ml Aβ42 oligomers for 15 min at 37° C. in 5% $CO_2$. 0.5 μg/ml human EGF (Sigma) was used as a positive control. Cells were then washed with PBS for 3 times and collected.

Western Blot Analysis

Whole fly head or cells lysates were prepared using a RIPA buffer containing 0.3% SDS, 50 mM Tris-HCl, pH 7.4, 0.5% NP-40, 1% sodium deoxycholate, 150 mM NaCl, 5 mM EDTA, 1 tablet per 50 ml complete protease inhibitor cocktail (Roche Diagnostics). Lysates were diluted in an SDS sample buffer and separated on 10-20% Tris-Tricine gels (Invitrogen), and transferred to nitrocellulose membranes (Invitrogen). The membranes were boiled in PBS for 3 min, blocked with 5% non-fat dry milk and blotted with a first antibody. First antibodies used herein included mouse anti-Aβ42 (6E10, Covance Research Products), mouse anti-dEGFR (Abcam), rabbit anti-hEGFR (Cell Signaling), mouse anti-hEGFR-p (Cell Signaling) and rabbit anti-Actin (Sigma). Data were analyzed with the ImageJ software (National Institutes of Health).

Immunoprecipitation

Protein G-agarose (Roche Diagnostics) beads were washed with PBS and RIPA buffer then conjugated with rabbit anti-hEGFR for 4 h at 4° C. Beads were then incubated with cell lysates overnight at 4° C. Cell lysates were removed after 3 times wash with RIPA. Beads were boiled at 100° C. for 5 min and loaded into 10-20% Tris-Tricine gels following standard Western blot protocols.

Mouse Strains and Genotyping

An AD-model mouse which expressed a mutant chimeric mouse/human APPswe and a mutant human presenilin 1 (Delta E9), both driven by the prion protein promoter, was purchased from the Jackson laboratory [strain B6C3-Tg (APPswe.PSEN1dE9) 85 Dbo/J]. Transgenic mice were derived from B6C3/Tg+×B6C3 crosses. Genotyping is done by PCR following the Jackson Laboratory protocols [primers for Tg(APP): 5' AAT AGA GAA CGG CAG GAG CA 3' (SEQ ID NO: 1) and 5' GCC ATG AGG GCA CTA ATC AT 3' (SEQ ID NO: 2); primers for Tg(PSEN1): 5' AGG ACT GAC CAC TCG ACC AG 3' (SEQ ID NO: 3) and 5' CGG GGG TCT AGT TCT GCA T 3' (SEQ ID NO: 4)]. Tg+ and their Tg− littermates were randomly assigned to various groups for drug treatment or vehicle control.

Morris Water Maze

The Morris water maze experiment was performed following a procedure as previously reported (Jensen et al., *Neuroscience* 130: 667-684, 2005; Cohen et al., *Cell* 139: 1157-1169, 2009). Briefly, littermate 8-month-old mice (30-40 g in weight) were placed one animal per cage and fed in normal conditions. A water tank with 120 cm in diameter was filled with room temperature water (19-20° C.), which was made opaque with white paint. A transparent platform (Φ 15 cm) was located in the center of one of the four virtually divided quadrants and was submerged 2 cm below the water surface to be invisible. Distal cues were provided in all experiments as spatial references. Mice were let swim until they found the platform and allowed to stay for 5 seconds; if a mouse did not find the platform, it was gently guided to the platform and given the 5 s stay. Animals that did not find the platform were given a latency of 60 s. Mice were allowed to rest for 1 h between trials. Four trials were performed each day. In all experimental settings, a video tracking system was utilized (Jiliang Software Technology Co. Ltd., Shanghai, China). Latency to find the platform (maximum of 60 s) was recorded for each trial and the four daily trials were averaged for statistical analysis. For drug treatments, Gefitinib was dissolved in 0.5% Tween-80 in physiological saline. Lavage of weight-matched drug diluted in physiological saline was carried out once each day from nine days before training and testing till the end of experiments.

Statistical Analysis

All data were analyzed by student t test or one-way ANOVA following Bonferroni test (Origin version 8; OriginLab Corporation). Statistical results are presented as means±s.e.m. or as individual data (horizontal line) and mean (small square). Asterisks indicates critical values (*P<0.05, P<0.01 and *p<0.001).

Example 2

Results

Ameliorating the Aβ42-Induced Early Memory Loss by Inhibition of the EGFRs in Transgenic Fruit Flies and Mice.

Experiments were conducted to determine whether insulin receptor (InR) and epidermal growth factor receptor (EGFR) mediated signaling pathways were involved in Aβ42-induced memory loss. First, an experiment was done to determine the effect of pan-neuronal overexpression of normal InR and EGFR, respectively, in Aβ42 transgenic flies.

Different genotypes of 5-day-old female adult flies were assayed for learning scores through well-established classic aversive conditioning (Tully and Quinn, *J Comp Physiol A* 157: 263-277, 1985), in which an odor was paired with foot-shocking. In 5-day-old transgenic female flies, expression of Aβ42 had no detectable memory loss while over-expressing InR or EGFR (elav-Gal4/+; UAS-InR$^{wt}$/+ or elav-Gal4/+; UAS-EGFR$^{wt}$/+) had very little effect on the memory performance (FIG. 1A). In contrast, co-expression of EGFR with Aβ42 (elav-Gal4/+; UAS-Aβ42/+; UAS-EGFR$^{wt}$/+) produced a synergistic effect in reducing the immediate memory, whereas co-expression of InR with Aβ42 (elav-Gal4/+; UAS-Aβ42/UAS-InR$^{wt}$) yielded a memory score similar to over-expression of InR alone (FIG. 1B). Such genetic interaction data implies that increased EGFR activity, instead of InR, might be relevant in causing the Aβ42-induced memory loss.

Figure 2:
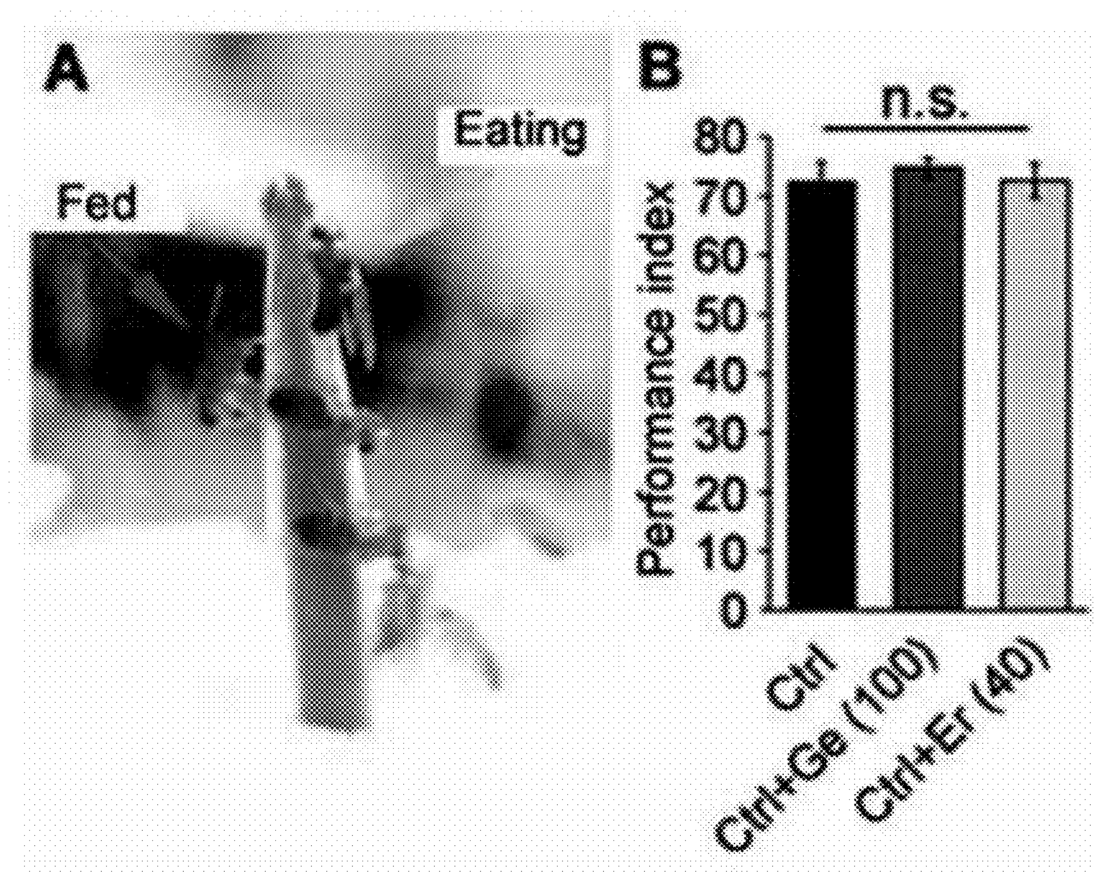
FIG. 2A-B. Toxicity of EGFR inhibitors on memory ability of fruit flies. (A) A red food colorant was dissolved in drug solution for indicating the fed flies. Green arrow points to a fly eating the drug; red arrow points to a fly finished eating (red abdomen). (B) No significant memory toxicity of two used EGFR inhibitors was found compared with control flies (+/Y; UAS-Aβ42/+) treated with sucrose. Concentrations (in μg/ml): 100 for gefitinib (Ge) and 40 for erlotinib (Er). N=8.

To validate this genetic observation, we tested effects of two EGFR inhibitors, gefitinib (Ge) and erlotinib (Er), which are used in clinical cancer therapy (Gschwind, et al., *Nat Rev Cancer* 4: 361-370, 2004). Both drugs inhibit the tyrosine kinase activity of EGFR via binding with the ATP-binding sites which are highly conserved between fruit flies and humans (Birnbaum and Ready, *Curr Treat Options Oncol* 6: 75-81, 2005). For the purpose of seeing a stronger memory-loss phenotype, we selected 3-day-old male adults (elav-Gal4/Y; UAS-Aβ42/+) for drug treatment. Memory scores were measured at day 10 of post-eclosion following 4 hours drug feeding each day for 7 consecutive days (Chiang, et al., *Proc Natl Acad Sci USA* 107: 7060-7065, 2010) (FIG. 1C and FIG. 2A). It was intriguing to note that memantine, the clinically available drug for AD treatment, was capable of preventing the memory loss in Aβ42-expressing flies (FIG. 1C). Feeding of either EGFR inhibitor also prevented the memory loss in 10-day-old Aβ42-expressing males over a range of concentrations (0.01, 0.1, 1, 10 μg/ml; FIG. 1C). Memory was not affected in control flies fed with higher concentrations of either Ge (100 μg/ml) or Er (40 μg/ml) (FIG. 2B). Behavior data suggest that inhibition of EGFRs prevents the Aβ42-induced memory loss in *Drosophila*.

Figure 3:
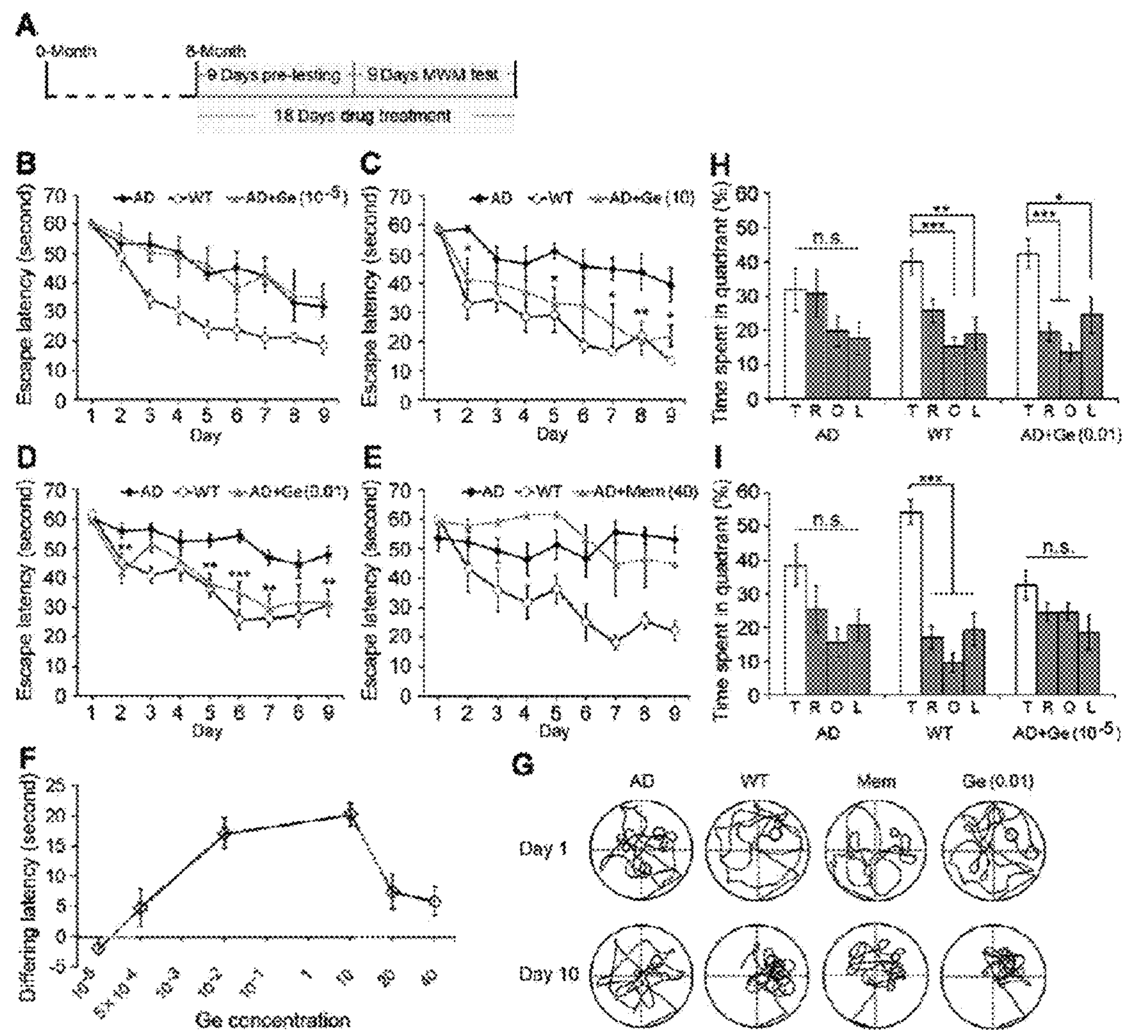
FIG. 3A-I. Rescue of Aβ-induced memory loss via pharmacological inhibition of EGFR in mice in Morris water maze (MWM) test. (A) Drug feeding skim to 8-month old double transgenic mice. Drug dosage is specified in each figure as mg/kg/day. (B-D) Memory rescuing effect through treatment of Ge at different concentrations. (E) No improvement in memory after Mem treatment. N=6-8 in B; N=6-7 in C; N=12-16 in D; N=6-8 in E. (F) Dosage effect of Ge in memory rescuing effects. Escape latency results from Day 7 to 9 were included for calculation. Ge is effective at very low concentrations. (G) Representative swimming traces for probe trails on day 1 and day 10. (H-I) Memory rescue is also evident in the test of removed submerged stand as indicated by time spent within different quadrant. Control (WT) and drug treated mice spent more time in platform-located target quadrant (ANOVA, *p<0.05, p<0.01, *p<0.001). T, target; R, right; 0, opposite; L, left.

To determine general significance of such observations, we tested effects of Ge, which penetrates the blood brain barrier and has some effectiveness in treating brain tumors (Ceresoli et al., *Ann Oncol* 15: 1042-1047, 2004; Heimberger et al., *Clin Cancer Res* 8: 3496-3502, 2002), in Tg(APPswe.PSEN1dE9) double transgenic mice with the expression of two mutated AD-linked transgenes: a chimeric human amyloid beta (A4) precursor protein (APPswe) and a "DeltaE9" mutant of human presenilin 1 (Jankowsky et al., *The Biomolecular Engineering* 17: 157-165, 2001). Extensive plaques are reported to be visible in early ages and the memory-loss phenotype is evident around 6-9 months old double transgenic mice (Jankowsky et al., *The Biomolecular Engineering* 17: 157-165, 2001; Reiserer, et al., *Genes Brain Behav* 6: 54-65, 2007; Savonenko et al., *Neurobiol Dis* 18: 602-617, 2005; Cohen et al., *Cell* 139: 1157-1169, 2009; Jankowsky et al., *J Neurosci* 25: 5217-5224, 2005). The Morris water maze was used for the behavioral assay, in which mice learned to find a hidden platform (Martinez-Coria et al., *Am J Pathol* 176: 870-880, 2010). Although two-month drug feeding (from 6- to 8-month-old) produced a positive effect, only 9-day pre-training drug treatment (FIG. 3A) was sufficient to rescue the memory loss in 8-month-old (FIG. 3). In contrast, with such short period of treatment, memantine was unable to improve the memory-loss phenotype (FIG. 3E), although it is reported to be effective with much longer of treatment (Martinez-Coria et al., *Am J Pathol* 176:870-880, 2010; Scholtzova et al., *J Neurosci Res* 86:2784-2791, 2008). Ge was most effective when administered at concentrations between 0.01 and 10 mg/kg/day (FIG. 3B-D, F), which is hundreds, if not thousands, of times lower concentration than that used for treating tumors in mice (Heimberger et al., *Clin Cancer Res* 8:3496-3502, 2002; Wakeling et al., Cancer Res 62:5749-5754, 2002). This is also consistent in the plot of representative paths (FIG. 3G) and in quadrant occupancy times (FIG. 3H-I).

Aβ42 Oligomers-Induced Activation of EGFRs.

Figure 4:
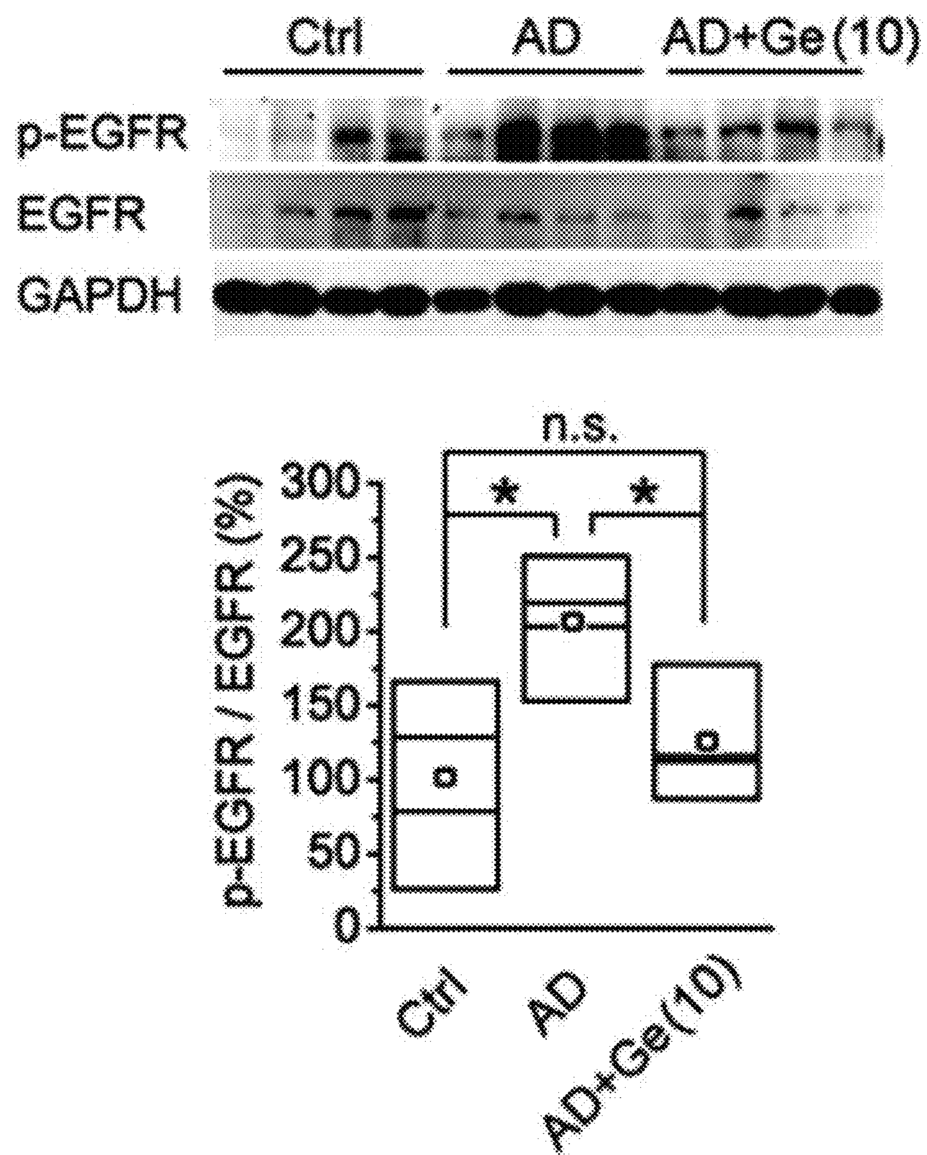
FIG. 4. Increased phospho-EGFR levels and its suppression through Ge treatment in the hippocampus of double transgenic mice. In 12-month old mouse hippocampus, the relative p-EGFR level in double transgenic mice was significantly increased compared with control. Feeding with 10 mg/kg/day Ge for 18 days suppressed the elevated EGFR activation. Top panel: representative Western blotting. Lower panel: individual data (horizontal line) and means (small square) are shown (same presentation of Western blotting for following figures). N=4.

To determine molecular mechanisms underlying observed genetic and pharmacological effects of EGFR in Aβ-induced memory loss, we assayed the level of EGFR activation in hippocampus region through western blotting of p-EGFR$^{Tyr1068}$, the site for binding with Grb2 that leads to activation of MAPK (Rojas, et al., *J Biol Chem* 271:27456-27461, 1996). The p-EGFR level was significantly increased in hippocampus of the double transgenic mice (FIG. 4). Importantly, the increased p-EGFR level was brought back to a level similar to the control after 18 days (the duration used for memory rescue) of Ge treatment (10 mg/kg/day, FIG. 4), showing that elevated EGFR activity correlated well with the Aβ-induced memory loss.

Figure 5:
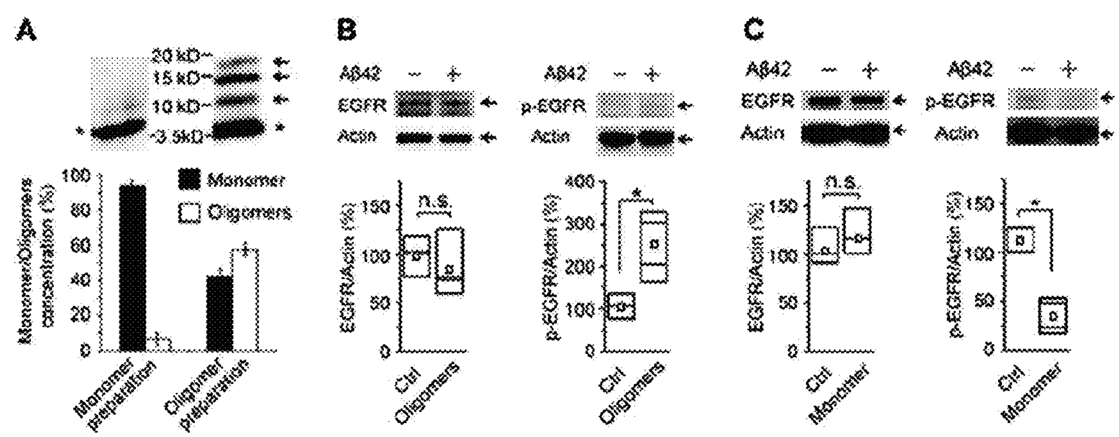
FIG. 5A-C. Monomeric Aβ42 inhibits EGFR activity while oligomers enhance EGFR activity. (A) Top panel: prepared Aβ42 peptides were separated by 10-20% tricine gels and immunoblotted with 6E10 antibody. Star shows monomer while arrows indicate oligomers. Lower panel: statistical results indicate different abundance of momers and oligomers in different preparations. (B-C) COS-7 cells were not transfected with human $EGFR^{wt}$ and Aβ42 plasmids. Endogenous p-EGFR and EGFR levels were detected. Incubation with 25 μg/ml monomeric or oligomeric Aβ42 for 15 min induced opposite effects on EGFR activation (right panels), while total EGFR levels were not influenced (left panels). N=3-4. In this and following figures, Western blotting results are expressed as individual data (horizontal line) and means (small square) are shown.
Figure 6:
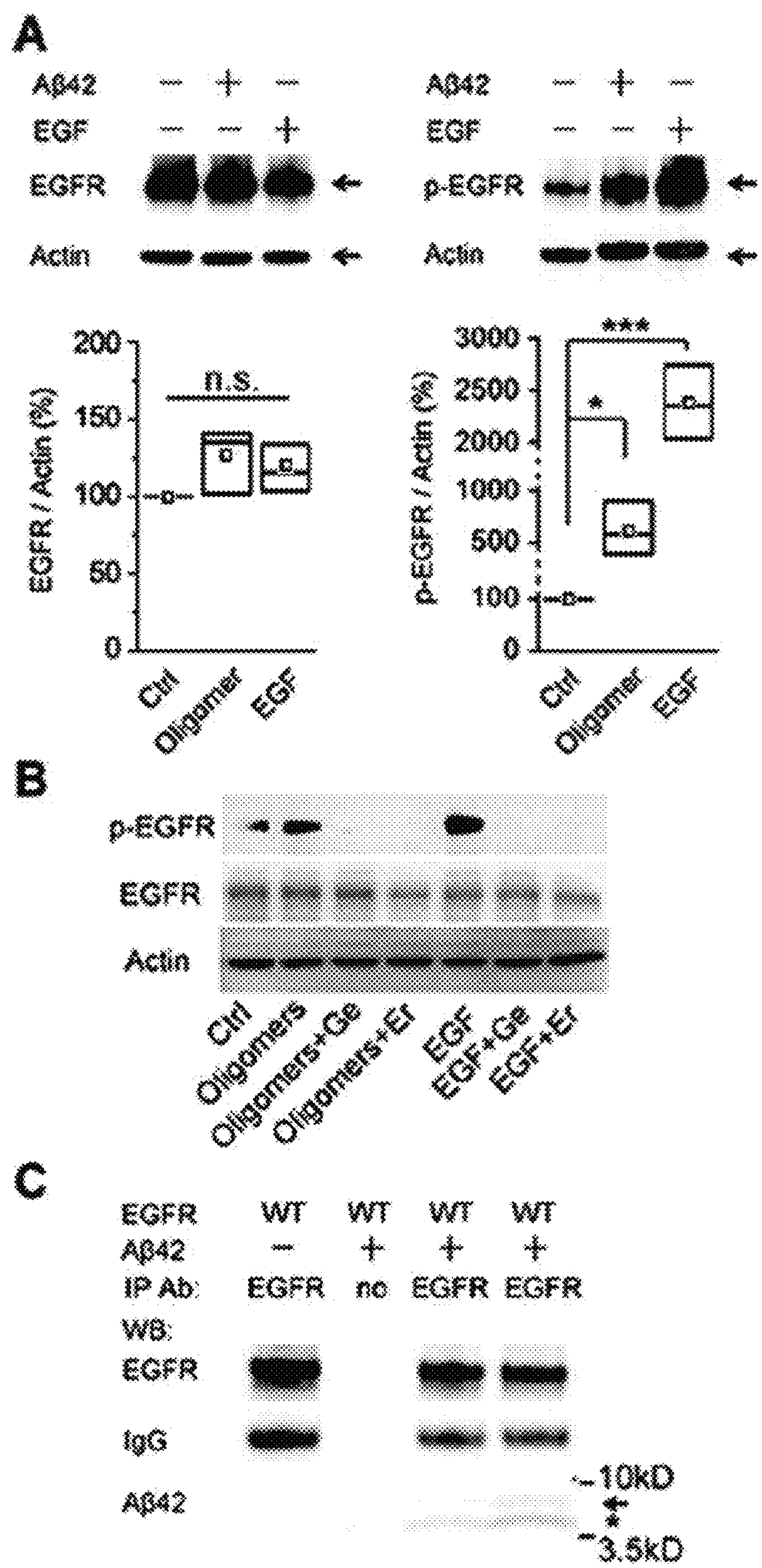
FIG. 6A-C. Oligomeric Aβ42 activates and co-precipitates with EGFR in cultured cells. (A) Elevated p-EGFR (right), but not total EGFRs (Left), in response to oligomeric Aβ42 and EGF application. COS-7 cells were transfected with human $EGFR^{wt}$ plasmid for 48 h, then incubated with 25 μg/ml oligomeric Aβ42 preparation for 15 min. Human EGF (0.5 μg/ml) for positive control. N=3. (B) Inhibition of Aβ42- and EGF-induced activation of p-EGFR by EGFR inhibitors Ge and Er, respectively. (C) Co-precipitation of Aβ42 with EGFRs. COS-7 cells were transfected with Aβ42 and human $EGFR^{wt}$ plamids for 48 hr, then cell lysates were incubated with protein G-agarose beads conjugated with rabbit anti-EGFR for immunoprecipitation. Monomer (star) and dimer (arrow) of Aβ42 are visible.

In order to make sure EGFR activation was caused by expressed Aβ, we measured p-EGFR levels in cultured COS-7 cells, a cell line derived from monkey kidney with low background affinity with Aβ42 (Lauren et al., *Nature* 457: 1128-1132, 2009), transfected with human wild-type EGFR ($EGFR^{wt}$). Western blotting showed that although expression levels of EGFRs were not affected after application of 25 μg/ml Aβ42 from oligomeric preparation (FIG. 5A), the level of p-EGFR or activated EGFR was significantly elevated (FIG. 5B and FIG. 6A). In contrast, treatment with monomeric Aβ42 preparation had an opposite effect on EGFR activation (FIG. 5C). EGFR inhibitors, Er and Ge, suppressed both EGF- and Aβ42 oligomers-activated EGFR (FIG. 6B).

To gain further insights into such Aβ-induced activation of EGFR, we performed immunoprecipitation to determine if endogenously produced Aβ42 could directly bind to EGFRs. COS-7 cells were co-transfected with genes encoding a secretory form of Aβ42 and a human $EGFR^{wt}$. Cell lysates were assayed for co-immunoprecipitation with rabbit anti-EGFR 48 hours later. We found that both Aβ42 monomers and oligomers, probably dimers according to the molecular weight, were pulled down with $EGFR^{wt}$ (FIG. 6C).

Taken together, these data support the notion that EGFR functions as a cell membrane receptor of Aβ peptides, and that Aβ oligomer-induced activation of EGFR plays a critical role in memory loss.

As shown above, the egfr gene, not the insulin receπtor gene, interacted with Aβ42 toxicity genetically. Further, both Gefitinib (Ge) and erlotinib (Er) were shown to rescue Aβ42-induced age-dependent memory loss in a *Drosophila* AD model. Moreover, Ge also rescued memory loss in a mouse model of AD which expressed an AD-related APP gene mutant together with an AD-related precenilin gene mutant. Aβ42 was also shown to increase the phosphoryλation and activation of EGFRs in cultured COS-7 cells, and that Aβ42 molecules were immunoprecipitated with EGFRs.

Taken together, these data indicate that excessive expression of Aβ42 leads to abnormal activation of EGFRs, which in turn activates downstream pathways, such as PI3 kinase-mediated signaling pathway, which then affects synaptic plasticity that ultimately causes memory loss. Inhibition of this Aβ42-induced direct activation of EGFR rescues memory loss in both *Drosophila* and Aβ-based AD mouse models. As shown above, EGFR inhibitors (Ge and Er) did not affect learning in normal animals, but rescued memory loss in AD animals. Notably, rescuing effects were observed after AD mice were fed with Ge for only seven days, suggesting that the drug acted on mechanisms mediating acute toxicity of Aβ42 in causing memory loss. In contrast, a drug currently marketed for treating AD, momentine, had no effect after an eighteen-day treatment in the study. Furthermore, the effective concentrations of Ge in rescuing memory loss were one hundred to one thousand times lower that that used for the treatment of cancers. Therefore, the use of Ge at an effective dosage for treating AD would be expected to have minimal side-effects.

What is claimed is:

1. A method of treating memory loss in a subject suffering from Alzheimer's disease, comprising administering an effective amount of an epidermal growth factor receptor ("EGFR") inhibitor to said subject, wherein the EGFR inhibitor is Gefitinib or Erlotinib.

2. The method of claim 1, wherein the EGFR inhibitor is Gefitinib and is administered to the subject at a dose of 1 to 100 mg/day/person.

3. The method of claim 1, wherein the EGFR inhibitor is administered to the subject via oral or parenteral administration.

* * * * *